US007953267B2

(12) United States Patent
Zellerhoff

(10) Patent No.: US 7,953,267 B2
(45) Date of Patent: May 31, 2011

(54) METHOD FOR THE THREE-DIMENSIONAL REPRESENTATION OF A STRUCTURE INFLUENCED BY A PERIODIC PROCESS, AND MEDICAL IMAGING SYSTEM

(75) Inventor: Michael Zellerhoff, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 977 days.

(21) Appl. No.: 11/881,379

(22) Filed: Jul. 26, 2007

(65) Prior Publication Data

US 2008/0025590 A1 Jan. 31, 2008

(30) Foreign Application Priority Data

Jul. 28, 2006 (DE) ......................... 10 2006 035 067

(51) Int. Cl.

| | |
|---|---|
| ***G06K 9/00*** | (2006.01) |
| ***G06K 9/32*** | (2006.01) |
| ***A61B 6/00*** | (2006.01) |
| ***G01N 23/00*** | (2006.01) |
| ***G21K 1/12*** | (2006.01) |
| ***H05G 1/60*** | (2006.01) |
| ***H05G 1/10*** | (2006.01) |

(52) U.S. Cl. ........ 382/131; 382/128; 382/154; 382/294; 378/8; 378/21; 378/95

(58) Field of Classification Search ........................ None
See application file for complete search history.

(56) References Cited

U.S. PATENT DOCUMENTS 6,556,697 B1 * 4/2003 Bruder et al. ................. 382/131

FOREIGN PATENT DOCUMENTS

| | | |
|---|---|---|
| DE | 196 22 075 A1 | 11/1999 |
| DE | 199 46 092 A1 | 3/2001 |
| DE | 10 2004 057 308 A1 | 7/2006 |

OTHER PUBLICATIONS

Flohr et al., "Heart rate adaptive optimization of spatial and temporal resolution for electrocardiogram-gated multislice sprial ct of the heart", Journal of computer assisted tomography, vol. 25 Issue 6, pp. 907-923, Publication Date: 2001.*

Lauritsch et al., "Towards cardiac C-arm computed tomography", IEEE Transactions on Medical Imaging, vol. 25, No. 7, 2006, pp. 922-934.*

* cited by examiner

*Primary Examiner* — Tom Y Lu
*Assistant Examiner* — Thomas A Conway

(57) ABSTRACT

There is described a method for a periodic and three-dimensional representation of a periodically variable structure. A number of rotation images is generated for this purpose. The required rotations relating to the same event of the periodic process are started at intervals offset by a defined angle. From the rotation images, new image series are assembled with which three-dimensional representations relating to different phase ranges of the period are reconstructed.

19 Claims, 2 Drawing Sheets

METHOD FOR THE THREE-DIMENSIONAL REPRESENTATION OF A STRUCTURE INFLUENCED BY A PERIODIC PROCESS, AND MEDICAL IMAGING SYSTEM

CROSS REFERENCE TO RELATED APPLICATIONS

This application claims priority of German application No. 10 2006 035 067.7 filed Jul. 28, 2006, which is incorporated by reference herein in its entirety.

FIELD OF INVENTION

The invention relates to a method for the three-dimensional representation of periodic or periodically repeatable processes in the reconstruction of tomographic images of a structure from a number of projection images of the structure recorded from different recording angles, and a medical imaging system.

BACKGROUND OF THE INVENTION

In x-ray computer tomography used for medical purposes, a special procedure is used to calculate a three-dimensional image of an object from normal x-ray images, which do not contain any kind of depth information since they represent a projection of a three-dimensional object onto a two-dimensional surface. In this procedure, in one rotation, an imaging unit—e.g. comprising an x-ray tube and an x-ray detector—is rotated through at least 180° around the object and between 50 and 1000 projection images of the object are recorded in small angular increments and the respective angles of projection, also known as recording angles, are stored. A three-dimensional data record of the object can be obtained from these numerous projection images and recording angles by using special algorithms, e.g. the so-called filtered back-projection or ART (Algebraic Reconstruction Technique). The totality of the projection images that originate from the same rotation are also referred to below as "rotation images". Since projection images of which the angles of projection vary by 180° are mirror-symmetrical, the structure is captured completely by a rotation image around 180° (plus fanning angle of the x-ray tube).

This method is generally executed by means of specially constructed computer tomographs (CT devices).

For x-ray images in image-controlled diagnostic or surgical interventions on a patient, in which normal x-ray images are continuously recorded during the intervention, other x-ray devices—which permit good access to the patient—are often used. So-called c-arm systems, in which the x-ray tube and detector are arranged on the arms of a c-arm, which may be freely positioned around the patient, are favored in this case, said arms being situated opposite to one another. Even with such c-arm systems, tomographic images of the patient can be generated if necessary since the c-arm can likewise be positioned around the patient by approximately 180°.

By injecting a contrast agent, x-ray tomography can also be used to show tissues which, in their normal absorption behavior, are not distinguishable from their environment. If two rotations are carried out, with contrast agent being administered in only one rotation, and the image series then being subtracted from one another, the contrasted tissue, for example a vascular tree, can be reconstructed in isolation. This method is known as 3D subtraction angiography.

For the purpose of the reconstruction a large number of images is required from a rotation of at least 180°. Since the duration of the rotation is in the region of seconds (currently approx 4 to 8 seconds), physical functions such as heartbeat or respiration may result in localized blurring of the images, similar to motion blur such as is known from conventional photography.

Some physical functions can be recorded by simple methods and can be taken into account in the reconstruction. Such methods are described in DE 10 2004 057 308 A1.

A time-resolved representation of physical functions or of another time-dependent process has hitherto not been provided.

DE 196 22 075 A1 discloses a method and a device for the radiological investigation of individual cardiac phases of a patient, in which an x-ray beam bundle, which penetrates the heart of the patient in various angular positions within one half up to several rotations of the x-ray beam bundle around the patient, meets a beam receiver, wherein the cardiac rhythm of the patient is used to influence the rotation time of the x-ray beam bundle around the patient and to generate different control signals that are synchronized to the cardiac rhythm of the patient, so that radiological recordings of projections of different cardiac phases are possible.

SUMMARY OF INVENTION

An object of the invention, therefore, is to provide a method and an imaging system with which time-dependent, periodic or periodically repeatable processes can be shown in different phase ranges. In particular, said periodic or periodically repeatable processes may be heartbeat, respiration, intestinal contraction, a repeated injection of contrast agent or a repeated stimulation.

The invention achieves the object with the features of the independent claims. Preferred embodiments are described in the respective dependent claims.

According to the inventive method, at least two rotations are executed in succession around the periodically variable structure, wherein the starting angles of the rotation are suitably offset, whilst the rotations are preferably always started at a corresponding point in time, i.e. phase, of the periodic process.

The invention is based on the finding that a structure which is subject to periodically repeated or repeatable processes, and which is filmed several times through rotation images, the starting angles of which are offset with regard to one another by a defined angle, may be shown three-dimensionally and with time resolution. Through the use of projection images from different angle ranges that have been recorded in different rotations in the same phase range of the process, the time resolution can be increased.

The number of rotations is preferably adapted to the sequence speed of the process.

If N is the number of rotations, the starting angles of the rotations are preferably offset with regard to one another by approximately 180°/N. In this way the periodic process may be displayed with resolution after N phase ranges.

The rotations are preferably always started at the same phase in the periodic process, for example always at the beginning of an injection, or in the same phase of the cardiac or respiratory cycle.

In particular, the minimum of two rotations, during which rotation images are generated, are started by a signal from an ECG, an actuator—i.e. a stimulator, or an infusion pump; the periodicity may therefore be of natural or artificial origin. The start may be triggered by a significant event in the course of the signal, which always takes place in the same phase of the periodic process.

The method is particularly suitable for the display of processes on the heart, on the respiratory organs or on the digestive tract, as well as for muscle groups that may be periodically activated, or blood vessels or tissue such as the brain, in which contrast agent may be periodically injected. The aforementioned organs or tissues may be of human or animal origin.

If $t_c$ is a point in time respectively after the start of a rotation at which an image is to be reconstructed from the rotation images, T is the duration of a rotation and N is the number of said rotations, then such rotation images from the rotations that are made in the time $t_c-T/2N$ to $t_c+T/2N$, are used.

The invention is geared toward a corresponding medical imaging system, which is equipped with an imaging unit, a processor for reconstructing the projection images into tomographic images, and a control unit, and—preferably—having a signal input and an angle sensor. A starting signal for the rotation can be fed in through the signal input. The control unit guides the imaging unit. The reconstruction may be executed according to one of the methods described above.

The medical imaging system is preferably an x-ray c-arm system, which comprises the x-ray tube and the x-ray detector, said x-ray tube and x-ray detector being fixed to a c-arm, which may be freely positioned around an object, in particular a patient. The preferred embodiments of the invention are described below with reference to c-arm systems, but the invention may also be used analogously with computer tomographs.

The c-arm system can preferably start up a predefined starting angle and execute a complete rotation from each starting angle using the control unit and the angle sensor.

The signal input is preferably addressed electrically and can process the starting system so that the control unit initiates a rotation. The starting signal is preferably the signal from an ECG or similar measurement instrument for the recording and evaluation of sequences of an object of interest, a stimulator or an infusion pump.

BRIEF DESCRIPTION OF THE DRAWINGS

Preferred exemplary embodiments of the invention are now described below by way of example with the help of the accompanying diagrams, in which.

DETAILED DESCRIPTION OF INVENTION

Figure 1:
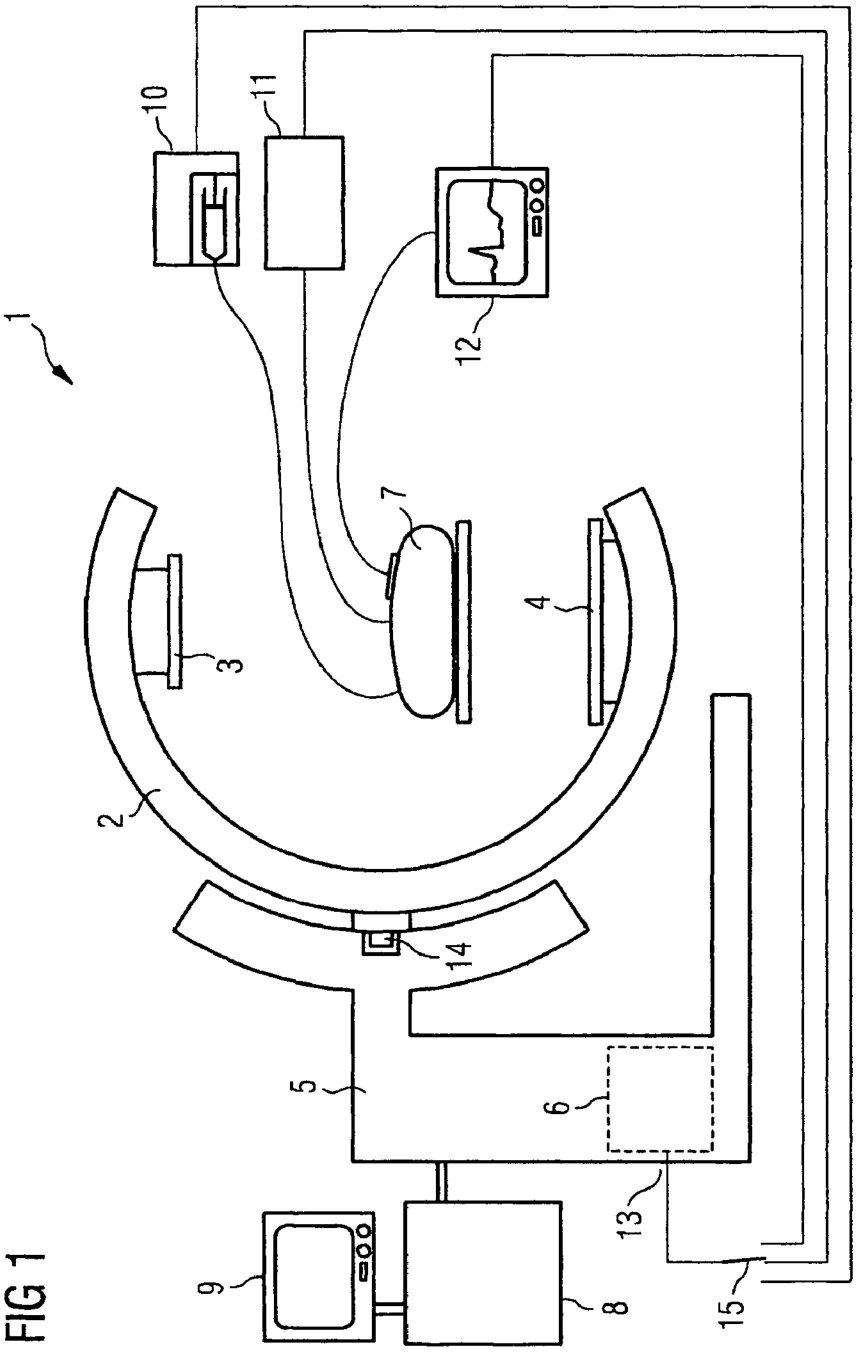
FIG. 1 shows a schematic view of a c-arm system, which is suitable for implementing an exemplary embodiment of the inventive method.

The invention is described below using the example of an x-ray c-arm system 1, in which a periodically variable structure 7, for example a patient, is positioned for investigation as shown schematically in FIG. 1. The x-ray tube 3 and the x-ray detector 4 are fixed opposite one another on the c-arm 2. The c-arm 2 is fixed to the stand 5 and may be freely rotated around the structure 7. During a pass of the c-arm 2 the structure 7 may be x-rayed from different projection angles 21.

From a plurality of such projection images, an image data processor 8 can reconstruct a three-dimensional image data record and display it on the monitor 9.

Figure 2:
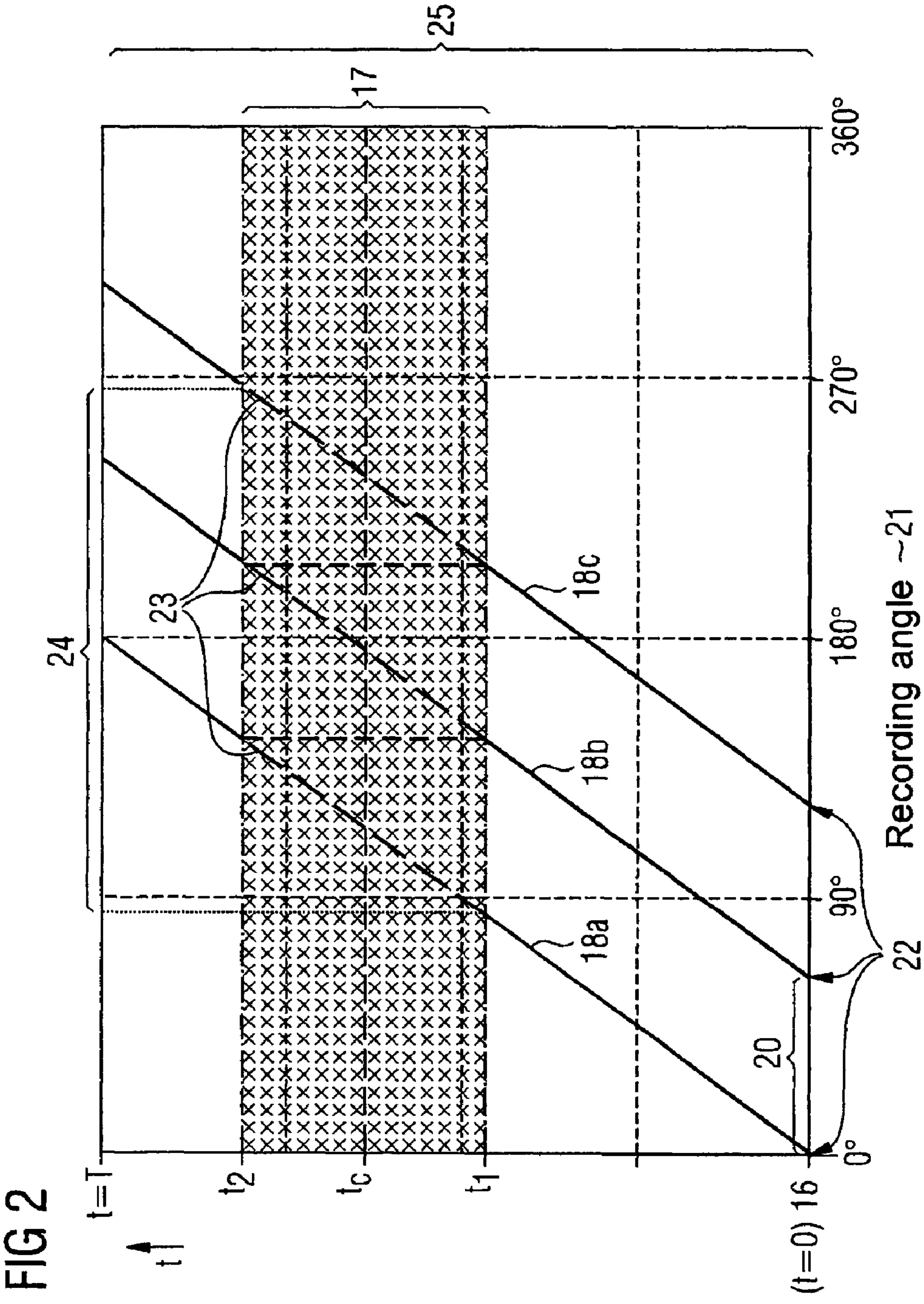
FIG. 2 shows a graphical depiction of the rotations with regard to the angle of projection for three rotations.

FIG. 2 shows a schematic representation of time t on the y-axis as opposed to the angle of projection on the x-axis. Each rotation is therefore shown by a dotted line 18*a*, 18*b*, 18*c*, which starts at t=0 and with a defined angle of projection, and ends at t=T (duration of a rotation, e.g. 5 s) and with a greater angle of projection.

After the number N of necessary rotations has been defined in particular according to the sequence speed of the periodic process and the traversing speed of the c-arm 2, from this information a differential angle 20 is calculated, the starting angle 22 is defined for each rotation, and the c-arm 2 is adjusted for the rotation by the control and regulation module 6 with the help of the angle sensor 14. Depending on which process is to be displayed, an infusion pump 10, a stimulator 11 or an ECG 12, or a similar measuring instrument for the recording and evaluation of sequences of the object of interest, is connected to the structure 7. The respective device is connected via a suitable signal output via a switch 15 to the signal input 13 of the x-ray c-arm system 1.

When a predefined trigger event occurs, in particular the commencement of an administration or when the minimum quantity of an infusion is exceeded, an excitation by the stimulator 11 or a specific signal sequence from the ECG 12 (e.g. the R waves) or from the similar measuring instrument for the recording and evaluation of sequences of the object of interest, the rotation is triggered at the point in time 16 and a rotation image 18*a*, 18*b*, 18*c* is generated.

In this way N rotation images are prepared with the offset starting angles 22. N may, for example, be 2, 3, 4, 5, 6, 7 or 8.

In FIG. 2 three rotations, 18*a*, 18*b* and 18*c*, have been shown respectively as a broad, solid line starting with the trigger point 16. After selection of a point in time to the phase range 17 of interest, as mentioned above, is defined as the interval around $t_c$.

Since the starting angles 22 of the rotations are offset with regard to one another by the differential angle 20, the angles of the projection images, at the point in time $t_c$, measured from the trigger point 16, are also offset by the differential angle 20.

In order to reconstruct the three-dimensional image data record of the process at the point in time $t_c$, all recorded images of the N rotation images 18*a*, 18*b* and 18*c* that have been made in a time interval (phase range 17) from $t_1=t_c-T/2N$ to $t_2=t_c+T/2N$, are combined into an image series, so that the image series comprises recorded images for all angles of projection in an angle interval 24 of 180°, but only from a phase range 17 of the periodic process with a duration of t/N. The interval between $t_1$ and $t_2$ is delimited in FIG. 2 by the dotted lines and the area hatched with "x". The angle sequence of the new image series 23 is indicated by a broad dotted line.

In order to show the periodic process, several points in time $t_c$ can be selected and a number of image data records (e.g. N) can be reconstructed according to the described method.

With this method, it is possible in particular for a beating heart or a tissue with dispersing contrast agent to be shown.

Since the patient's heartbeat may be assumed to be virtually periodic, the method shown may be used in order to reconstruct different phase ranges of a cardiac cycle. For cardiac imaging, the c-arm starts up the starting position for the respective rotation (e.g. for four rotations: 0°, 45°, 90° and 135°). The respective rotation can then commence, triggered by the specified event in the ECG signal.

As in the above example, the c-arm is moved to the respective starting position for the dynamic display of vascular circulation. The rotation may now be triggered by the infusion pump. A constantly equal quantity of contrast agent is preferably injected on each rotation. Since, in contrast to conventional 3D subtraction angiography, the vascular tree to be displayed does not have to be contrasted during the entire rotation, a significantly smaller quantity of contrast agent per rotation is sufficient.

The time resolution of the method is limited downward by T/N. If, therefore, a process with display resolution precise to one second is required, and if a device is available in which a rotation lasts for five seconds, then this may be achieved with five rotations and a differential angle 20 of 180°/5.

The invention claimed is:

1. A method for a three-dimensional representation of a structure moved or influenced by a periodic process, comprising:

rotating an imaging unit a predefined angular range of rotation about a structure, wherein N number of rotations comprising at least two rotations are executed in succession, wherein starting angles of the rotations have an offset with regard to one another based upon a predefined differential angle, wherein the predefined differential angle comprises the angular range of rotation divided by the N number of rotations;

recording a plurality of projection images for each N number of rotations from different projection angles between a starting angle and an end angle during rotation of the imaging unit in accordance with the predefined differential angle;

for a selected point in time $t_c$ after starting each N number of rotations, defining a time interval of $t_1$ to $t_2$ to include a phase range of interest of the periodic process based on the N number of rotations, wherein an interval duration is T/N, wherein $t_1=t_c-T/2N$ and $t_2=t_c+T/2N$, wherein T is a duration of a rotation, and wherein N is the number of the rotations;

combining into an image series of during the time interval of $t_1$ to $t_2$ representing the phase range of interest; and reconstructing a three-dimensional image data record based upon projection images assigned to the phase range, wherein the three-dimensional image data record shows the structure in the phase range of the periodic process.

2. The method as claimed in claim 1, wherein the structure is displayed with time resolution, and wherein the structure is a part of the human body or an animal body, and wherein the periodic process, is of natural or artificial origin.

3. The method as claimed in claim 1, wherein at least two rotations are triggered based upon the periodic process or based upon an actuator, wherein the actuator controls the periodic process.

4. The method as claimed in claim 1, wherein the periodic process has a measurable characteristic event, wherein the measurable characteristic event always takes place in the same phase of the periodic process, and wherein the rotation is triggered based upon the measurable characteristic event.

5. The method as claimed in claim 1, wherein the periodic process is selected from the group consisting of a heartbeat, a respiration, an intestinal contraction, a repeated injection of contrast agent, a artificial stimulant, and a combination thereof.

6. The method as claimed in claim 1, wherein the structure is selected from the group consisting of a blood vessel, a heart, a lung, a intestine, a muscle, a brain and a combination thereof.

7. The method as claimed in claim 1, wherein the periodic process is a heartbeat, wherein an ECG is recorded in a human or an animal body, and wherein at least two rotations are triggered based upon the ECG.

8. The method as claimed in claim 1, wherein at least two rotations are recorded respectively during:

an injection of a contrast agent into a human body or an animal body, or an artificial stimulation of the human body or the animal body.

9. The method as claimed in claim 1, wherein the predefined angular range for each rotation covers 180° between the starting angle and the end angle.

10. The method as claimed in claim 1, wherein the predefined angular range is 180° and the differential angle is 180°/N with N rotations.

11. The method as claimed in claim 1, wherein the image data record is reconstructed based upon all of the rotations, and wherein projections recorded in the same phase range of the periodic process are assigned to one another.

12. The method as claimed in claim 11, wherein each image data record is reconstructed based upon projection images with projection angles covering an angular range of at least 180°.

13. The method as claimed in claim 1, wherein the projection angle is stored for each projection image.

14. The method as claimed in claim 1, wherein the projection images are recorded with recording equipment of a x-ray device with a c-arm.

15. A medical imaging system, comprising:

an image-recording unit comprising an x-ray tube, and an x-ray detector, wherein a recording device is rotateable a predefined angular range of rotation around a structure, wherein the structure is moved or influenced by a periodic process, and wherein the recording device records a series of projection images from different projection angles between a starting angle and an end angle during N number of rotations around the structure;

a processor to reconstruct a three-dimensional image data record from the projection images of each rotation, wherein a three-dimensional image shows the structure in the same phase range of the periodic process, and wherein the reconstructed three-dimensional image is based upon the projection images respectively assigned to a phase range; and a control unit to control the image-recording unit, wherein the control unit guides the image-recording unit to execute N complete rotations in succession comprising at least two rotations, wherein the starting angles of the rotations are respectively offset with regard to one another by a predefined differential angle, wherein the predefined differential angle comprises the angular range of rotation divided by the N number of rotations, wherein the control unit allocates projection images from the rotations respectively to a phase range of the periodic process in a time interval from $t_1$ to $t_2$ defined to be based on the N number of rotations, wherein an interval duration is T/N, wherein:

$$t_1=t_c-T/2N,$$

$$t_2=t_c+T/2N,$$

$t_c$ is a point in time respectively after the start of each rotation at which an image is to be reconstructed from the rotation images, T is the duration of a rotation, and N is the number of said rotations.

16. The imaging system as claimed in claim 15, wherein the starting angle of each rotation is freely selectable, wherein a complete rotation of at least 180° is executed beginning from each starting angle, wherein an angle sensor indicates the recording angle with regard to each projection image, and wherein a control device controls the starting angle based upon the angle sensor.

17. The imaging system as claimed in claim 15, wherein a speed in an angle range between the starting angle and the end angle is essentially constant.

18. The imaging system as claimed in claim 15, wherein a signal input is used to trigger the rotation.

19. The imaging system as claimed in claim 18, wherein the signal input processes a signal selected from the group consisting of:

a sensor signal, a status signal from an actor, a trigger signal from an actuator, a trigger signal from an ECG, and a trigger signal from a measuring instrument to record and evaluate sequences of the structure.

* * * * *